United States Patent
Melnyk

(10) Patent No.: US 7,099,015 B2
(45) Date of Patent: Aug. 29, 2006

(54) FIBER OPTIC SENSING DEVICE FOR MEASURING A PHYSICAL PARAMETER

(76) Inventor: Ivan Melnyk, 604 Cottonwood Ave., Coquitlam, BC (CA) V3J 2S4

(*) Notice: Subject to any disclaimer, the term of this patent is extended or adjusted under 35 U.S.C. 154(b) by 451 days.

(21) Appl. No.: 10/647,176

(22) Filed: Aug. 25, 2003

(65) Prior Publication Data

US 2005/0046862 A1  Mar. 3, 2005

(51) Int. Cl.
*G01B 9/02* (2006.01)
*G01J 3/45* (2006.01)
*G01J 1/10* (2006.01)

(52) U.S. Cl. .................. 356/480; 356/454; 356/243.1; 356/479

(58) Field of Classification Search .............. 356/480, 356/451–456, 243.1–243.8, 479, 519; 250/339.07, 250/339.08, 339.09
See application file for complete search history.

(56) References Cited

U.S. PATENT DOCUMENTS

| | | | | |
|---|---|---|---|---|
| 5,303,165 A | * | 4/1994 | Ganz et al. .................. 356/319 |
| 5,392,117 A | * | 2/1995 | Belleville et al. ........... 356/480 |
| 6,078,706 A | * | 6/2000 | Nau et al. ................... 356/35.5 |
| 6,138,082 A | * | 10/2000 | Wang et al. ................. 356/319 |
| 6,621,574 B1 | * | 9/2003 | Forney et al. ............... 356/301 |
| 6,897,951 B1 | * | 5/2005 | Womble et al. ............. 356/301 |
| 6,901,176 B1 | * | 5/2005 | Balachandran et al. ....... 385/12 |
| 2005/0151975 A1 | * | 7/2005 | Melnyk ..................... 356/480 |

* cited by examiner

*Primary Examiner*—Hoa Q. Pham
*Assistant Examiner*—Patrick Connolly
(74) *Attorney, Agent, or Firm*—Oyen Wiggs Green & Mutala LLP; Richard A. Johnson

(57) ABSTRACT

A fiber optic sensing device uses a Fabry-Perot cavity to sense a physical parameter. The cavity modulates the incident polychromatic light. The modulated light is recorded by an optical spectrometer means. The spectrum is analyzed in a signal processing unit which normalizes the spectrum and determines the phase of the modulated signal. The phase, accumulated over whole range of wavelengths, has been used for identification of the physical parameter using a look-up-table. The cavity, the polychromatic light source and the spectroscope means are connected by fiber optic means.

16 Claims, 15 Drawing Sheets

FIBER OPTIC SENSING DEVICE FOR MEASURING A PHYSICAL PARAMETER

BACKGROUND OF THE INVENTION

The present invention relates to fiber optic sensing technology, and more specifically to a sensor and method using a Fabry-Perot optical interferometer and spectral signal demodulation for measurement of a physical parameter such as a pressure, a temperature, a strain, and a refractive index with a high accuracy and within a large range of physical parameters.

Fiber optic interferometric sensors offer a number of advantages over electrical sensors such as inherent immunity to electromagnetic interference, capability of operating in harsh environments and at longer distances, miniature sizes, etc. A fiber optic Fabry-Perot sensor typically consists of a measuring Fabry-Perot probe, a fiber optic extension cable and an opto-electronic module. The measuring Fabry-Perot probe represents a cavity with two partially reflective surfaces. The cavity modulates the spectrum of the incident light depending on cavity spacing and the refractive index of the media inside the cavity. Both, the cavity spacing and the refractive index define the optical path difference between the beams that are reflected from each reflective surface at certain wavelength. The optical path difference determines the conditions for maximums and minimums of the spectral modulation, which is changed with the physical parameter. The extension cable connects the probe to the opto-electronic module by means of transmitting the light from the light source to the probe and transmitting the modulated light back to the opto-electronic module for demodulation and further signal processing. The opto-electronic module includes a light source and a fiber optic coupling means for connecting the light source to the extension cable. The probe can be connected directly to the opto-electronic module if a long distance is not required.

Light sources which produce a broad spectrum light (polychromatic or white light sources) are cheap and less susceptible to thermal instability. They are preferred to be used in fiber optic sensors for wide industrial applications where the typical operating temperature is ranging from −40 C to +60 C. The returning light is demodulated in the opto-electronic module either by means of a second interferometer or by spectral means. Interferometric demodulation provides low signal-to-noise ratio unless mechanical scanning of the reference mirror is provided. Precise mechanical scanning may be done only in a stabilized environment which is costly to achieve and maintain. Spectral demodulation does not require mechanical scanning. It can be achieved by using conventional microspectrometers which have miniature size and robust design. Fiber optic spectroscopes are primarily based on diffractive gratings which provide linear spectra along the wavelengths. Modern diffractive gratings, in particular, holographic diffractive gratings have high efficiency and resolution along wide range of spectrum.

A number of techniques have been proposed for improving fiber optic interferometric sensors with spectral demodulation. U.S. Pat. No. 6,577,402, MILLER, Jun. 10, 2003 discloses a fiber optic interferometric sensor with spectral demodulation which is based on comparison of spectral light intensities taken at two wavelengths with the reference values recorded for the same wavelengths. The wavelengths are preferably selected at zero crossing locations where the spectral modulation has the highest contrast. Such a technique may be applied only for sensing the physical parameter within a narrow range. This range is limited by a half-period of the spectral modulation, and if the modulated optical spectrum shifts beyond its reference location, the two-point technique will indicate the value of the physical parameter which corresponds to the shift calculated from another fringe of the modulated spectrum.

A technique described in U.S. Pat. No. 6,141,098, SAWATARI et al., Oct. 31, 2000 is based on recording a calibration set of modulated spectra and comparing the measured spectrum with the calibration set. The modulated spectrum is normalized by subtracting the reference fringe pattern from the actual data fringe pattern, and then dividing by the average intensity of the reference pattern. However, such way of normalization requires both measuring and calibration conditions to be identical, which is difficult to achieve in practice. The measuring spectrum is changed with the fiber length, and also, from one opto-electronic module to another because of the spectral variability of the light sources. The deviation of the real measuring condition from the calibration condition, which is seen from the fluctuation of the average value in the referred document, leads to the higher inaccuracy because the measuring spectrum could not match with any stored calibrated data.

Another fiber optic interferometric sensor utilizing spectral decoding is described in U.S. Pat. No. 4,945,230, SAASKI et al., Jul. 31, 1990 and related documents. The sensor is based on a Fabry-Perot sensing interferometer with a very short optical path (two mirrors in a Fabry-Perot cavity are located closely). The interferometric pattern in such an arrangement has only one minimum which shifts with the physical parameter. The position of the interferometric minimum changes the proportion of light from each side of the minimum which can be registered by two photodetectors. Although simple, this method also has limited measuring range because the physical parameter can be measured within the fraction of a single fringe.

Also known in the art is the document TAPIA-MERCADO, et al., "Precision and sensitivity optimization for white-light interferometric fiber optic sensor", J. Lightwave Technol., v. 19, 2001, pp. 70–74 describing a zero-crossing technique in Sagnac fiber optic temperature sensors. The procedure of analyzing the shift in the interferometric pattern which includes determining the position of zero crossing points is based on normalization of the recorded spectra by calculating the two auxiliary spectra which are found by interpolating the maxima and minima of smoothed recorded spectrum. However, the interpolation error is increased with the smaller number of fringes in the spectrum and, consequently, the accuracy of the determination of the zero-crossing points is reduced.

Yet known in the art is the document EGOROV et al., "High reliable, self calibrated signal processing method for interferometric fiber-optic sensors", SPIE, v. 2594, 1996, pp. 193–197 describing a method for signal demodulation. The method is based on converting the optical spectrum into the optical frequency domain, calculating the Fourier transform of the converted signal, filtering the oscillating component, calculating the inverse Fourier transform and calculating a derivative of the final phase spectrum which gives the absolute value of the optical path difference. The conversion of the spectra from wavelength to optical frequency domain requires a long computation time because it must include a number of splining operations in order to achieve acceptable accuracy. This complexity increases the response time of the sensor making it too slow for sensing some physical parameters. The algorithm must include tracking of the oscillating frequency which is changed with the physical parameter.

The value of the oscillating frequency is determined as a maximum in the amplitude part of the first Fourier transform which adds yet another complexity to the method and increases the response time of the sensor. No normalization has been proposed for this method based on assumption that spectral change of the light source will not affect the phase distribution.

Many applications require not only tracking the value of the sensing parameter, but measurement of the physical parameter in a large range. Such a requirement is typical of absolute temperature and pressure measurements for downhole applications in the oil and gas industry, or the measurement of strain in construction, etc.

Typically fiber optic sensors are installed in locations that are different from those where sensors were calibrated. The difference occurs due to the light attenuation in the extension cable, which can vary in length from one installation to another. Bending of the fiber affects the mode content which changes the intensity of the light coming to the optoelectronic module. Polychromatic light sources, such as LED's, in particular, usually have spectral power distributions that vary from unit to unit. Replacing the optoelectronic module requires recalibration of the probe. This is a complex task because it affects the sensing environment. For example, the recalibration of the pressure probe requires a depressurization of the pressurized vessel, which is associated with the interruption of the technological process. Recalibration is impossible in fiber optic strain sensors, which are used in construction because probes are permanently embedded into the concrete. Light sources are subjects to degradation with time and the aging reduces the total amount of light coming to the spectroscope, consequently causing the fluctuation of the average value. The latter introduces a systematic error in zero-crossing algorithms. Therefore, there is a need for a method and a sensor with a reliable normalization technique.

An object of the present invention is to provide a fiber optic sensing device based on white light interferometric method with spectral demodulation of the interferometric spectrum, for measuring a physical parameter within a range that is not limited by a single fringe of the modulated spectrum.

It is another object of the invention to provide such a fiber optic sensing device with a high accuracy and stability.

It is a further object of the invention to provide such a fiber optic sensing device with a possibility for in-field normalization of the signal and means for correcting the variation of spectral intensity of light caused by the bending of fibers and instability of the light source.

SUMMARY OF THE INVENTION

According to the present invention, a modulated spectrum from a fiber optic Fabry-Perot sensing interferometer is registered with a microspectrometer. The modulated spectrum consists of a number of interferometric fringes located within the spectral range of the polychromatic light source. Positions of the fringes are associated with the optical path difference defined by the gap spacing of the Fabry-Perot cavity. In the preferred embodiment, the positions of the fringes are determined by the phase of the modulated spectrum. The phase is calculated over the whole range of wavelengths, without conversion of the spectrum into the frequency domain. The phase gives information about the value of the measuring parameter. Preferably, the phase is calculated using the direct FFT, filtering the transformed data with a band-pass filter and performing the inverse FFT. The band-pass filter has fixed cut-off frequencies, which are determined from the minimum and maximum optical path differences of the sensing interferometer. Because the phase oscillates according to the fringe pattern, the accumulated phase is calculated over the whole range of wavelengths.

The method and a fiber optic sensing device utilizing this method, allow measurement of a physical parameter over a wide operating range as the accumulated phase integrates the phases calculated from all interferometric fringes. Also, the method and device provides higher accuracy than can be determined by the phase of a single fringe.

According to the present method, there is also provided an optical sensing method and a fiber optic sensing device for measuring a physical parameter, including a process for normalizing the optical spectrum. The normalization is provided by using a combination of normalization and measuring probes. The normalization probe provides the same attenuation of the optical signal as the measuring probe does without the modulation of the spectrum. The normalization probe allows measuring the spectrum of the polychromatic light source which may change with time. The normalization spectrum is used for calculation of the normalized signal by dividing the measuring spectrum over normalization spectrum. The phase of the normalized spectrum is determined; the phase is compared with the calibrated phase which is associated with the value of the physical parameter.

DETAILED DESCRIPTION OF THE PREFFERED EMBODIMENTS

Figure 1:
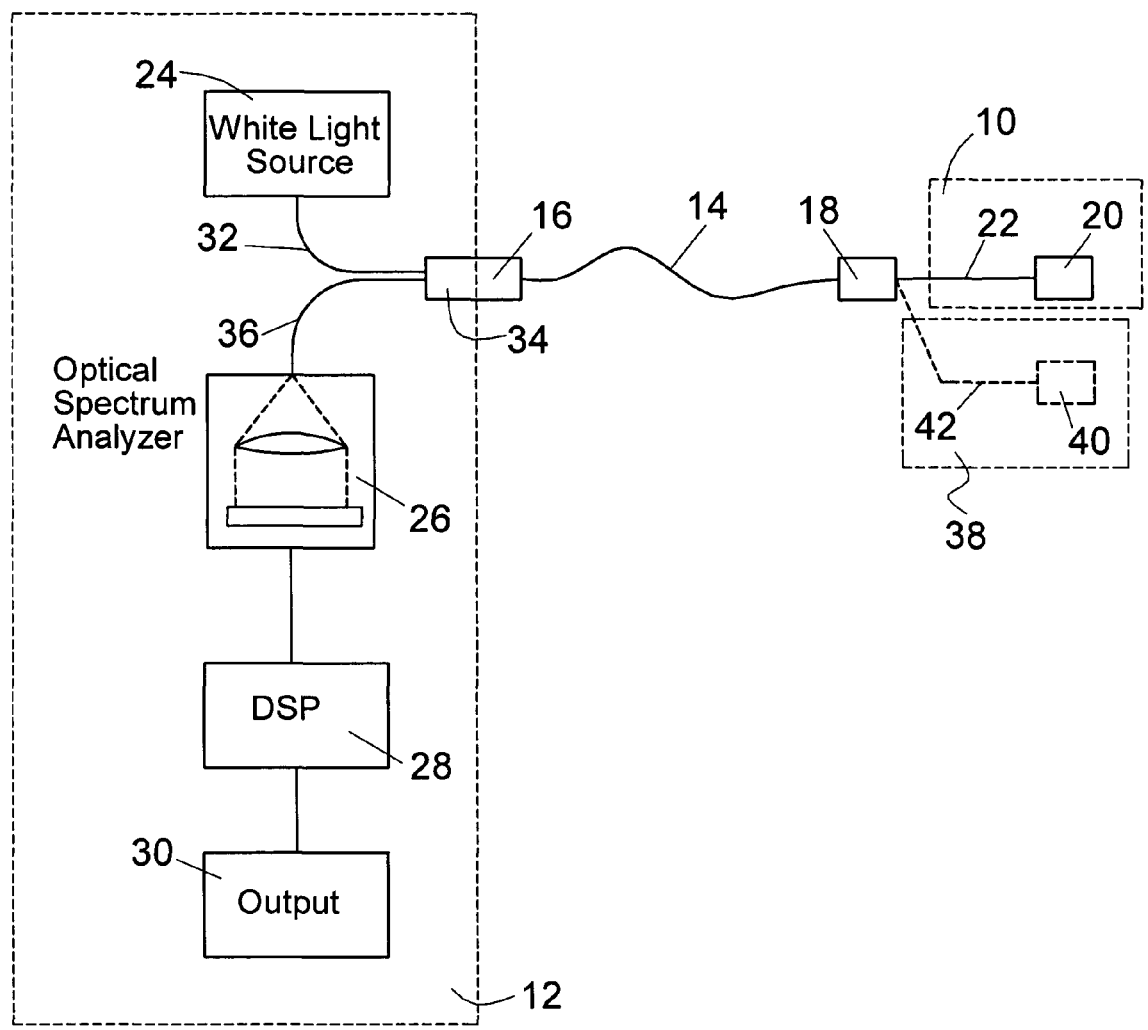
FIG. 1 is a schematic view of a fiber optic sensing device for measuring a physical parameter according to the present invention

Referring to FIG. 1, the fiber optic sensing device according to the present invention consists of a fiber optic measuring probe (10) connected to an opto-electronic module (12) either directly or through an extension cable (14). The connection is provided by the fiber optic connectors (16) and (18). The measuring fiber optic probe consists of a sensing interferometer (20) coupled with an optical fiber (22) to the connector (18). The sensing interferometer is preferably a Fabry-Perot interferometer, however, the invention may be applied to any kind of fiber optic interferometer which is used to modulate the spectrum of the light.

The opto-electronic module (12) consists of a polychromatic or white light source (24), an optical spectrum analyzer (26), a digital signal processing unit (28) and an output circuit (30). The opto-electronic module includes also a power supply unit (not shown) which delivers the electrical power to all opto-electronic parts above. Preferably, the opto-electronic module is powered by a 24 VDC power supply, which is a standard voltage for the industrial control systems. The polychromatic light source (24) delivers the light to the connector (16) via an illuminating fiber (32), which is coupled to the connector (16). The extension cable (14) may include a single fiber or a duplex fiber depending on the design of the sensing interferometer and its operation, either reflective or transmittive mode. For a single-fiber design, a fiber optic splitter (34) may be required for guiding the illuminating light into the extension cable, and deliver the receiving light into the receiving fiber (36). The optical spectrum analyzer (26) represents a microspectrometer with a linear CCD or CMOS detector array. The spectrometer registers the receiving light over a whole optical spectrum generated by the polychromatic light source. Preferably, the spectrometer is based on a diffractive grating. The grating spreads the light uniformly with wavelengths. Compact spectrometers using diffractive gratings, offer an optical resolution of a fraction of a nanometer. Alternatively, the spectrometer can be built using a linear variable filter, such as made by Optical Coating Laboratory Inc., CA. Such a filter has a multi-layer interference coating which selectively transmits the light along the filter without dispersing it angularly.

Before the measurement, a normalization fiber optic probe (38) can be attached to the connector (18) instead of measuring probe (10). The normalization probe has a reference element (40) attached to a fiber (42). The reference element together with the fiber (42) provides the same attenuation of the light as the measuring probe (10) without the modulation of the light by the sensing interferometer.

The digital processing unit (28) comprises a DSP microprocessor which is used to perform calculations further described below. The DSP may have a memory for storing calibrated, reference, measured, and calculated data. The final results are computed by the output circuit (30) to determine the value of the physical parameter and/or for communication with other control devices.

Figure 2A:
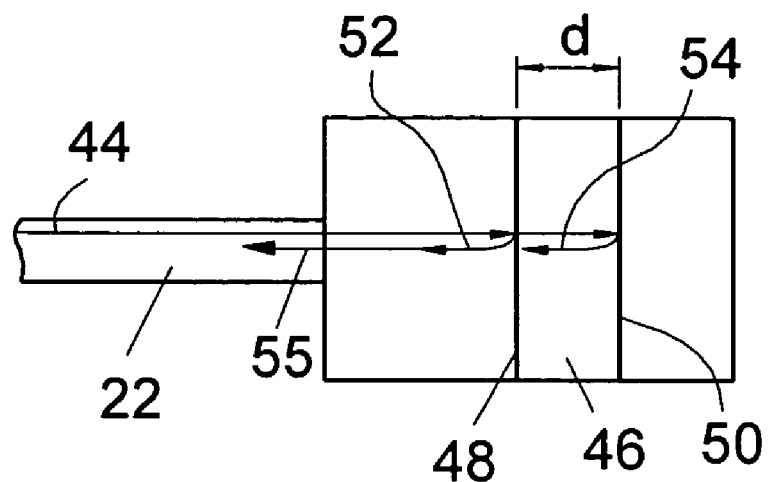
FIG. 2A is a schematic view of the reflective Fabry-Perot sensing interferometer used as an example of the measuring probe in the present invention.

Referring now to FIG. 2A, a schematic view of the measuring Fabry-Perot probe working in reflective mode is shown. An illuminating beam (44) passes through the fiber (22) and reaches the Fabry-Perot cavity (46). The beam is partially reflected from each side of the cavity (48) and (50), thus, an optical path difference (OPD) occurs between the reflected beams (52) and (54). The OPD depends on the cavity depth d and a refractive index n of the medium inside the cavity. The OPD defines the phase shift $\phi$ between the beams (52) and (54) as $$\varphi = \frac{4\pi d n}{\lambda}$$

where $\lambda$ is the wavelength. The intensity of the beam (55) reflected from the cavity back into the fiber (22) is proportional to the phase function $I(\phi)$, which is defined for the ideal Fabry-Perot cavity (a cavity without the light absorption at reflective surfaces) as $$I(\varphi) = \frac{F\sin^2(\varphi/2)}{1 + F\sin^2(\varphi/2)}$$

where $$F = \frac{4R}{(1-R)^2}$$

R is the reflective coefficient.

Figure 2B:
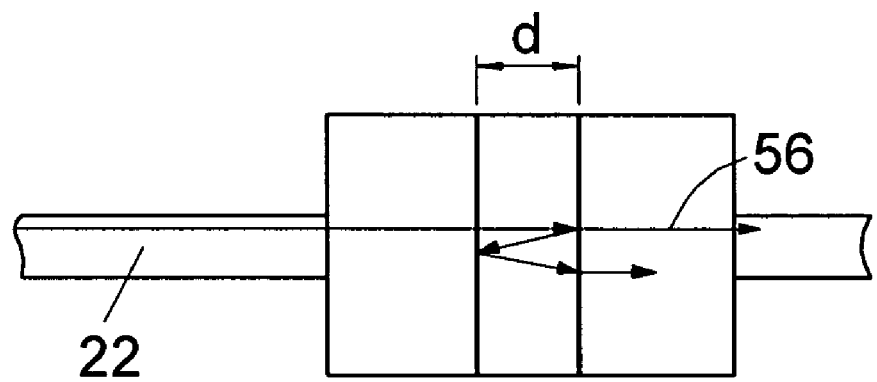
FIG. 2B is a schematic view of the transmittive Fabry-Perot sensing interferometer used as an example of the measuring probe in the present invention.
Figure 3A:
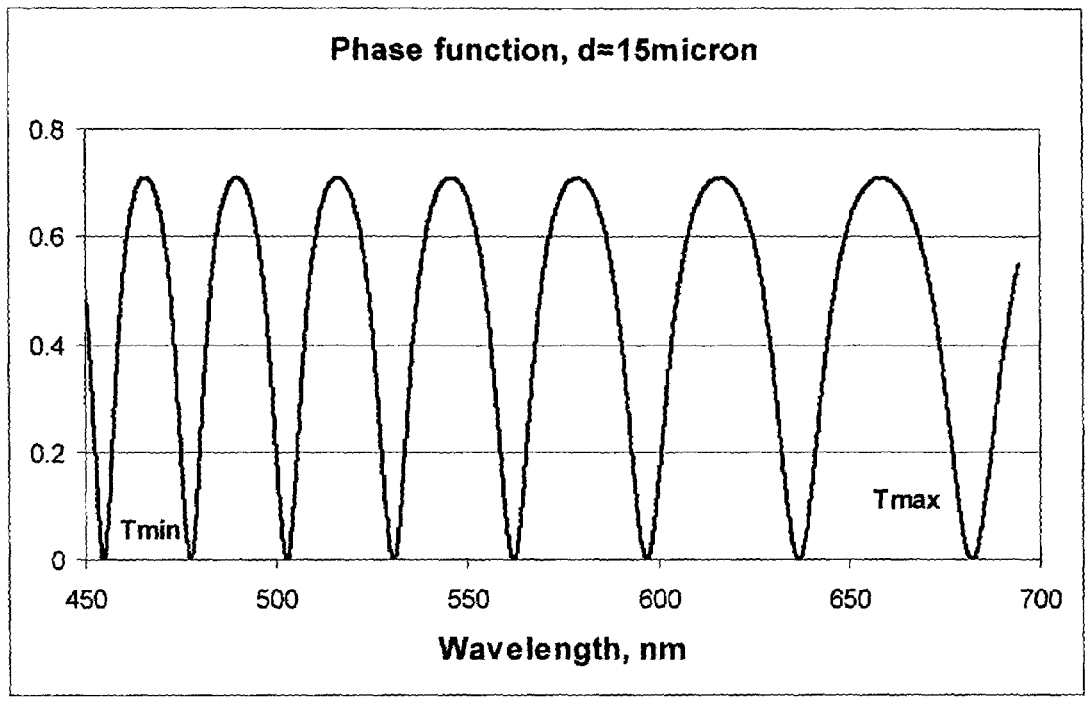
FIG. 3A is a view of the spectral phase function of the probe of FIG. 2A calculated for a Fabry-Perot cavity with 30% reflective surfaces displaced at 15 micron from each other.

A Fabry-Perot sensing interferometer can operate in transmittive mode such as shown in FIG. 2B. The phase function in transmittive mode is shifted by $\pi$ radians from that in reflective. In other words, the minimum intensity of the interfered beam (55) in reflective mode corresponds to the maximum intensity of the interfered beam (56) in transmittive mode and vice versa. An example of the phase function is shown in FIG. 3A; the phase was calculated for d=15 μm and R=30%. The phase function has an oscillating character, which is typical for an interferometric fringe pattern. It is also noticeable that the spacing between fringes increases with wavelength.

The phase function is changed as the physical measurement parameter causes the Fabry-Perot gap spacing to vary. For example, pressure typically causes the reduction of the gap d due to the deflection of the front mirror (50), whereas temperature or strain may increase or decrease d because of thermal expansion of the different materials, or because of mechanical stress, respectively. Changes of refractive index can also be measured if the sensed medium enters the cavity (46). Phase function is shifted along wavelengths if the measuring parameter is changed.

Figure 3B:
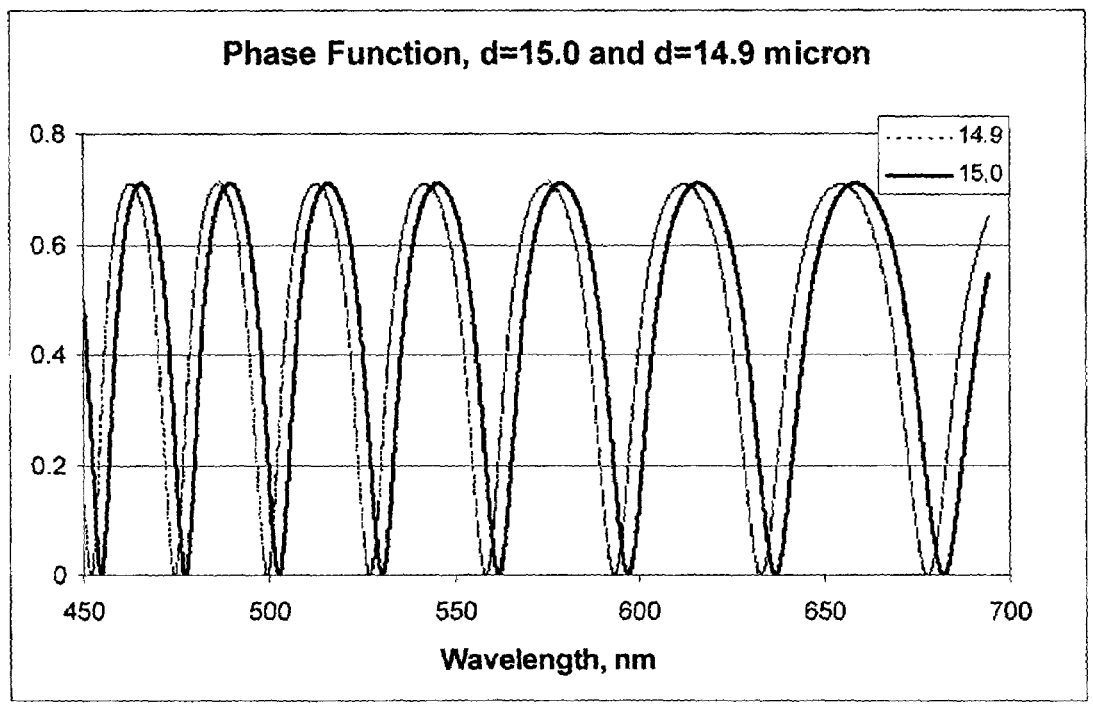
FIG. 3B is a view of the spectral phase function of FIG. 3A with the phase function, calculated for cavity depth of 14.9 micron.

According to the present invention, the phase function is used for identifying the measuring parameter. FIG. 3B shows two phase functions calculated for distances d=15.0 and d=14.9 micron. The phase function is shifted along the wavelength spectrum, if the measuring parameter is changed. The phase calculation includes the steps described below:

The spectrum of the incoming light from the light source $I_{LS}(\lambda)$ is modulated in accordance with the phase function $I(\phi)=I_{PF}(d,n,\lambda)$. The modulated spectrum of the light is registered by the spectroscope $I(\lambda)$, and is analyzed as the product of two spectra, the light source, $I_{LS}(\lambda)$ and the phase function $I_{PF}(d,n,\lambda)$:

$$I(\lambda)=I_{LS}(\lambda) \cdot I_{PF}(d,n,\lambda)$$

Figure 4:
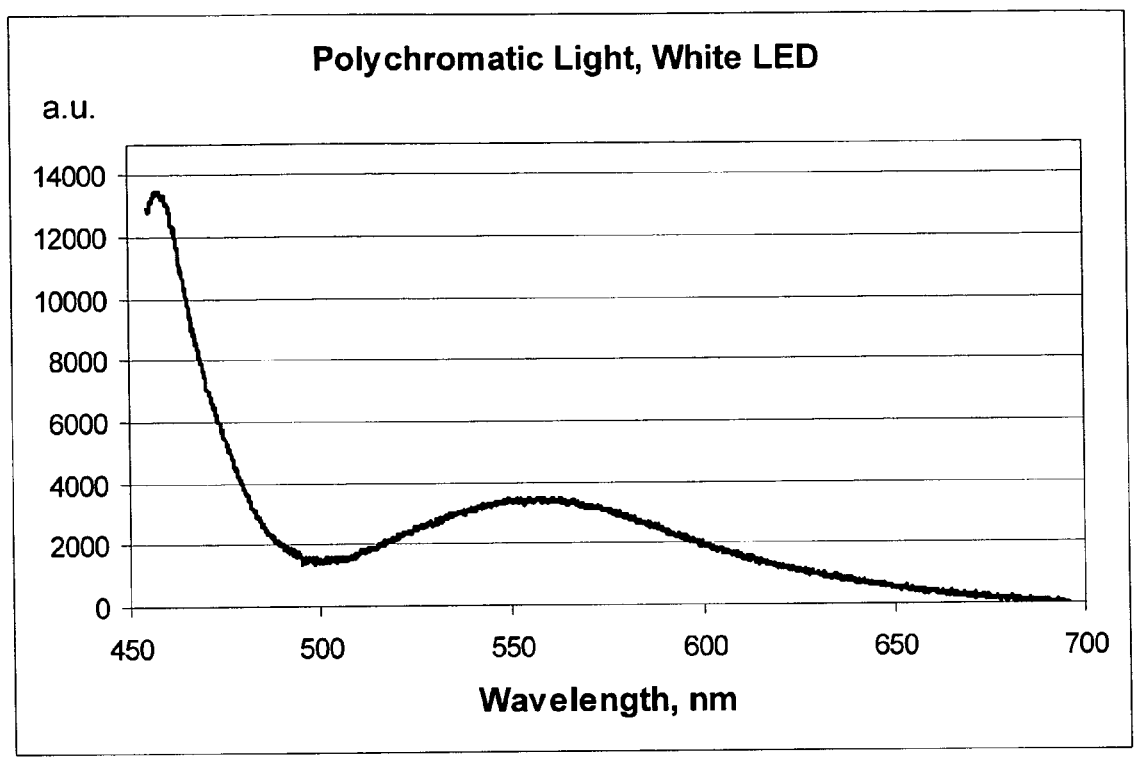
FIG. 4 is an example of the spectrum of white LED used as a polychromatic light source according to the present invention.

A polychromatic light source has a spectrum $I_{LS}(\lambda)$ extended over a wide range of wavelengths. The light source can be an incandescent lamp or a light emitting diode (LED). Incandescent lamps have limited lifetime. LED's are miniature and long lasting light sources with a half-spectrum of about 50 nm. White light LED's have an even wider spectrum approaching 200 nm. An example of the white LED spectrum is shown in FIG. 4. The spectrum has two maxima, one at 470 nm, which corresponds to the maximum emission of the blue excitation light, and a second at approximately 570 nm, which corresponds to the maximum emission of the yellow phosphor.

Figure 5:
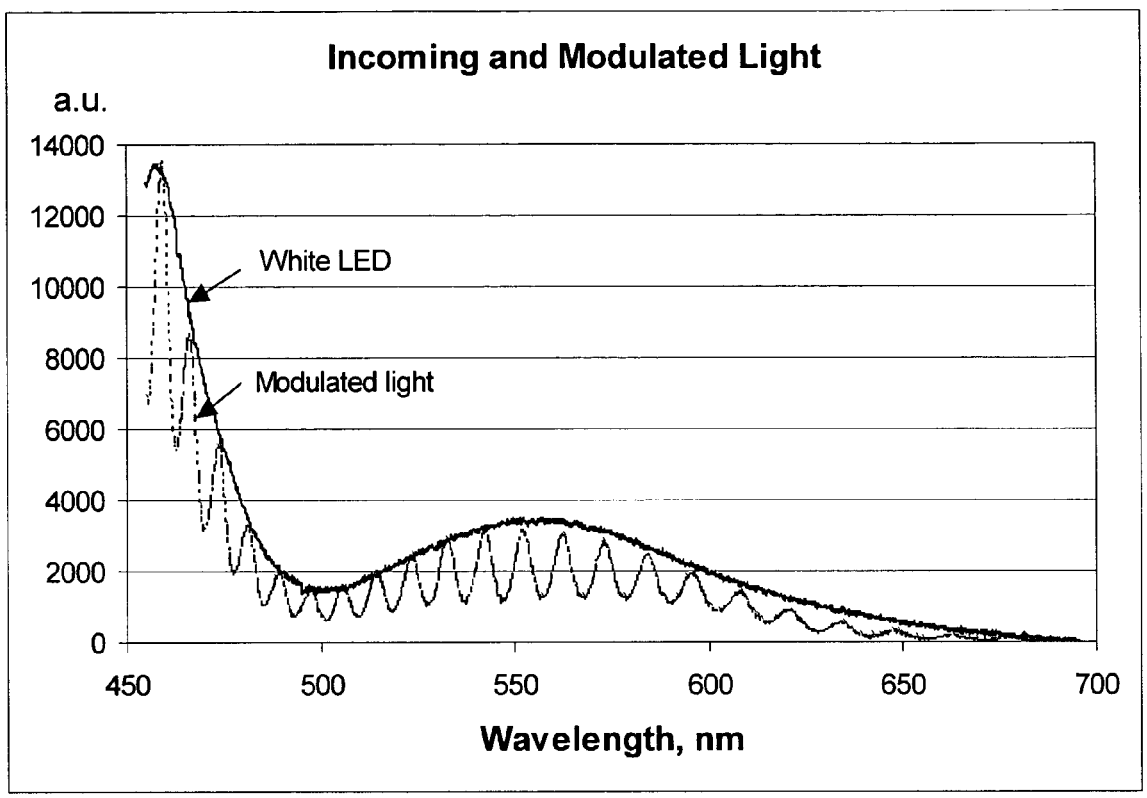
FIG. 5 is an example of the spectrum recorded from a sensing Fabry-Perot interferometer shown in association with an incoming spectrum of FIG. 4.

Referring further to FIG. 5, an example of the modulated spectrum $I(\lambda)$ is shown. The spectrum is presented together with the spectrum of the incoming light $I_{LS}(\lambda)$ from the white LED. FIG. 5 clearly indicates the complexity of the spectrum modulated by the sensing interferometer, which typically leads to variations of the average value and produces errors in the above referred zero-crossing demodulation technique.

Figure 6:
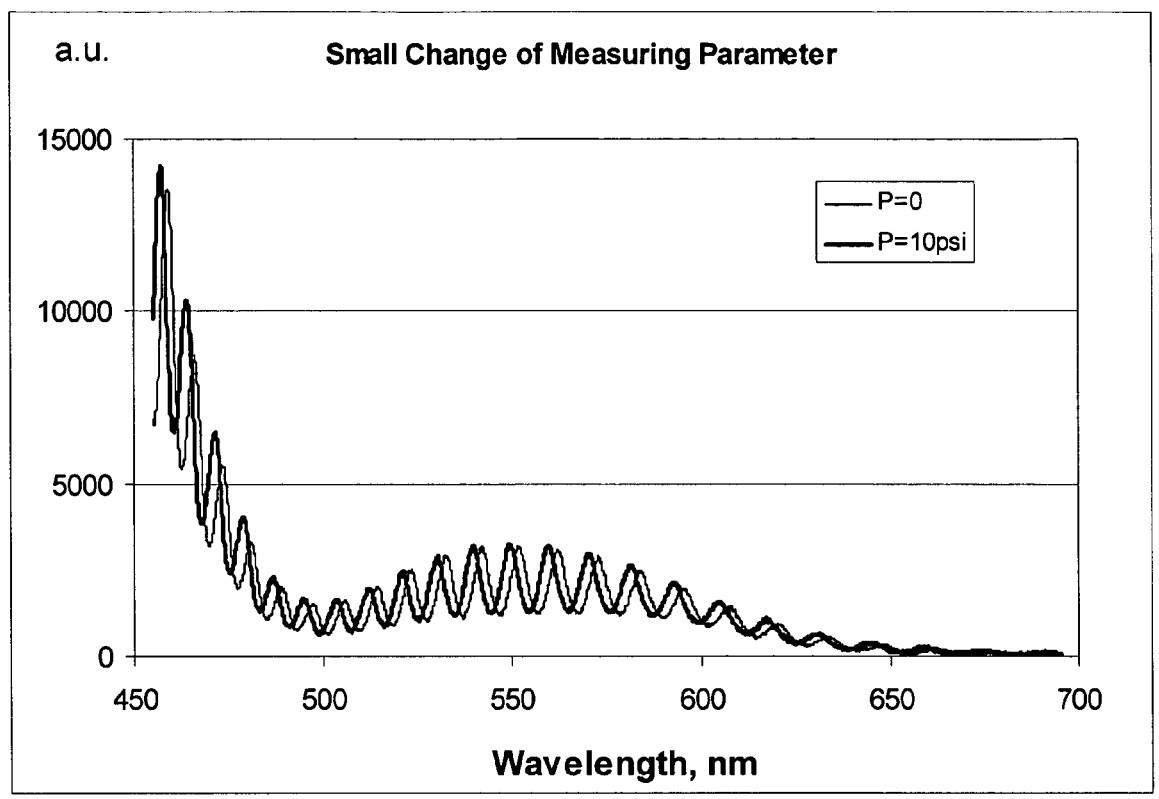
FIG. 6 represents two spectra of FIG. 5 recorded from a Fabry-Perot pressure sensor rated at a maximum pressure of 3,000 psi; spectra are recorded at two pressures that are close, P=0 and P=10 psi.

The interference pattern is shifted with the measuring parameter due to the change of the OPD. FIG. 6 shows two spectra, one recorded at external pressure of P=0 and another recorded at P=10 psi. In this example, the Fabry-Perot cavity was designed for a nominal pressure of 3,000 psi. A small change of the measuring parameter (pressure) causes a substantial phase shift of the interfered spectrum. This indicates the high sensitivity of the described method. According to FIG. 6, the shift exceeds a quarter of an interference fringe at shorter wavelengths. A quarter of a fringe is equivalent to a 90 degree phase shift, which can be detected with a high resolution.

Figure 7:
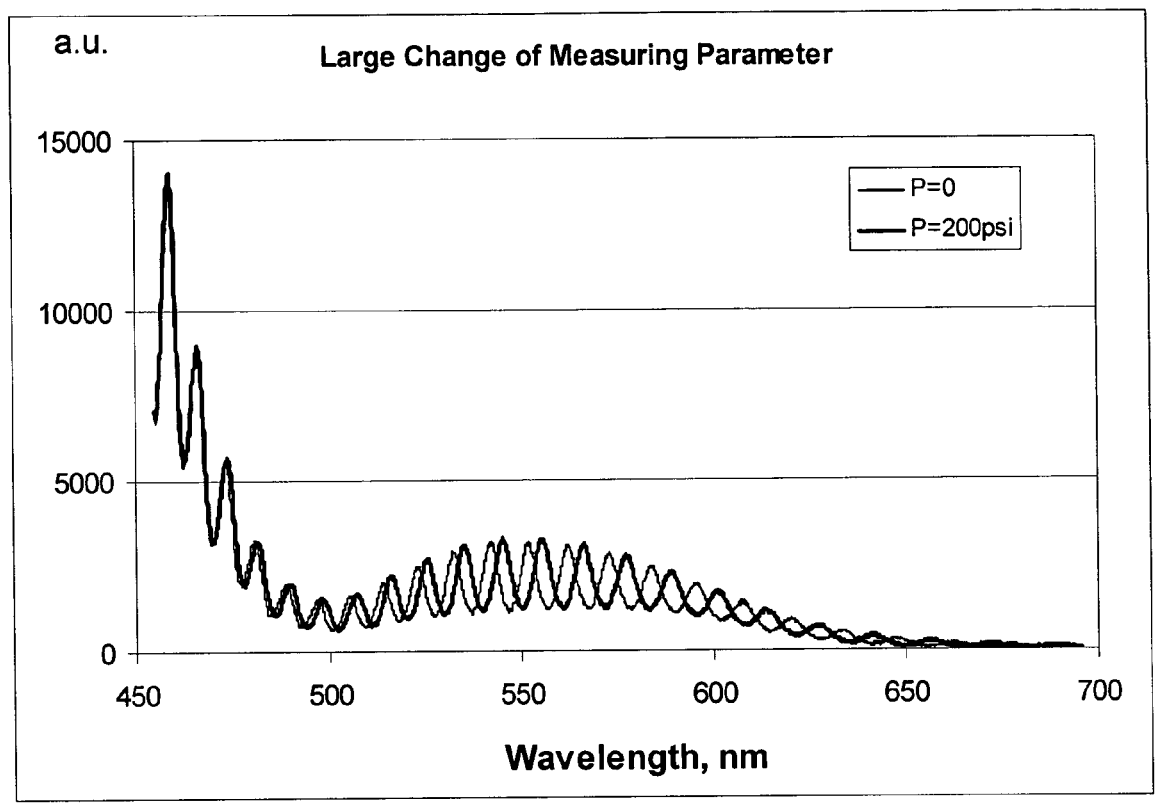
FIG. 7 represents two spectra of FIG. 5 recorded from a Fabry-Perot pressure sensor rated at a maximum pressure of 3,000 psi; spectra are recorded at two pressures, P=0 and P=200 psi.

Further change of the measuring parameter shifts the interference pattern beyond a single interference fringe. FIG. 7 contains the plot of spectrum recorded for the same probe at P=200 psi. The spectrum is shifted at such a degree that it is virtually overlapped at shorter wavelengths with the initial spectrum recorded at P=0. Both spectra become indistinguishable in a wide range of wavelengths.

According to the present invention, the phase of the modulated spectrum is determined in order to extend the measuring range. The phase is calculated from a normalized spectrum, which is determined as a ratio $$I_{norm}(\lambda) = \frac{I(\lambda)}{I_{LS}(\lambda)}$$

Figure 8:
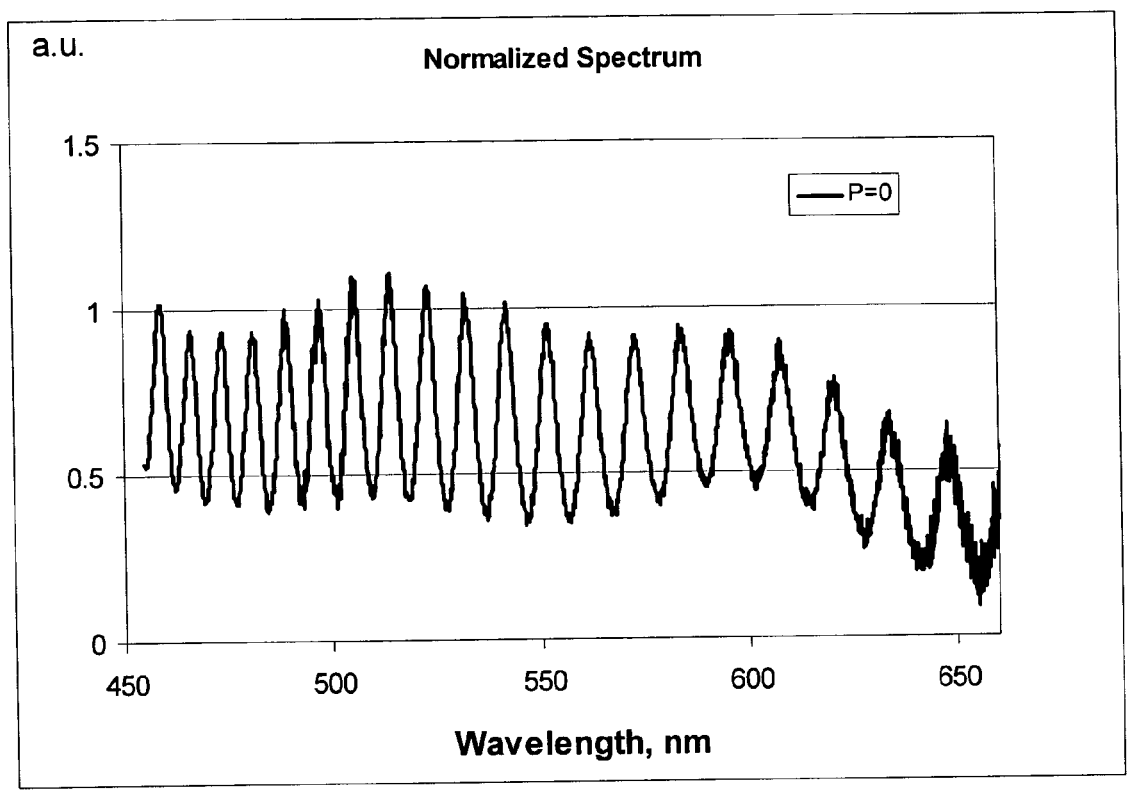
FIG. 8 is the view of the normalized spectrum calculated by dividing the measuring spectrum of FIG. 5 over the spectrum of the light source of FIG. 5.

An example of the normalized spectrum is shown in FIG. 8. This spectrum was calculated from data shown in FIG. 5 The spectrum contains a low frequency modulation and high frequency noise, which primary comes from the photodetector.

Figure 9:
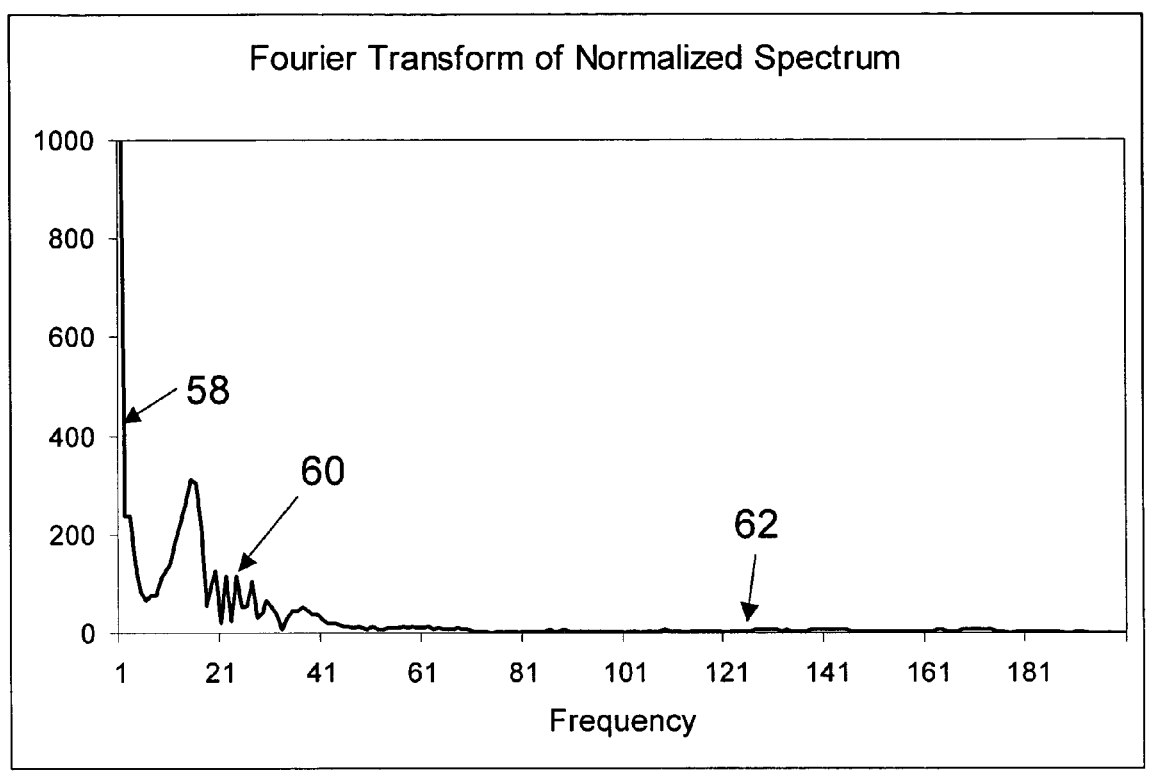
FIG. 9 is a view of the signal of FIG. 8 after direct FFT.
Figure 10:
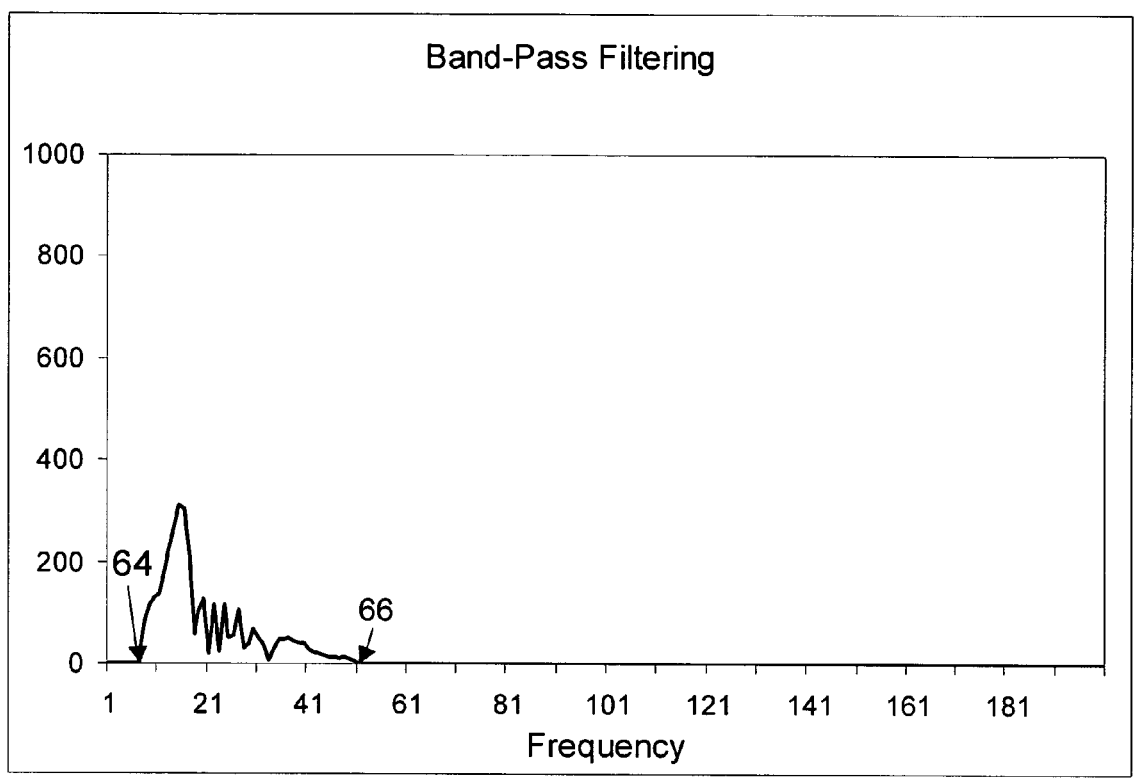
FIG. 10 is a view of the signal of FIG. 9 after band-pass filtering.

Further according to the present invention, a Fourier transform is performed on the normalized spectrum. FIG. 9 shows the result of the fast Fourier transform (FFT) from the normalized spectrum of FIG. 8. The amplitude portion of the FFT has a distinctive peak (58) at low frequency, a number of chirped peaks (60) corresponding to a modulated component of the spectrum, and a low-intensity high frequency noise (62) from the CCD. The FFT is filtered with a digital band-pass filter having a minimum (64) and a maximum (66) cut-off frequencies as is shown in FIG. 10. Preferably, the minimum and maximum cut-off frequencies are calculated as:

$$f_{\min} = \text{round}\left(\frac{N}{T_{\max}}\right);$$

$$f_{\max} = \text{round}\left(\frac{N}{T_{\min}}\right)$$

where N is the number of samples in the FFT, which is equal to the number of pixels in the CCD array, $T_{max}$ is the maximum fringe spacing shown in FIG. 3 which corresponds to the smallest OPD, $T_{min}$ is the minimum fringe spacing which corresponds to the largest OPD. Both $T_{min}$ and $T_{max}$ are defined based on the desirable range of measuring parameters. For example, $T_{min}$ is determined at shorter wavelengths of the spectrum calibrated at the lowest pressure $P_{min}$, whereas $T_{max}$ is determined at longer wavelengths of the spectrum recorded at highest detectable pressure $P_{max}$.

Figure 11:
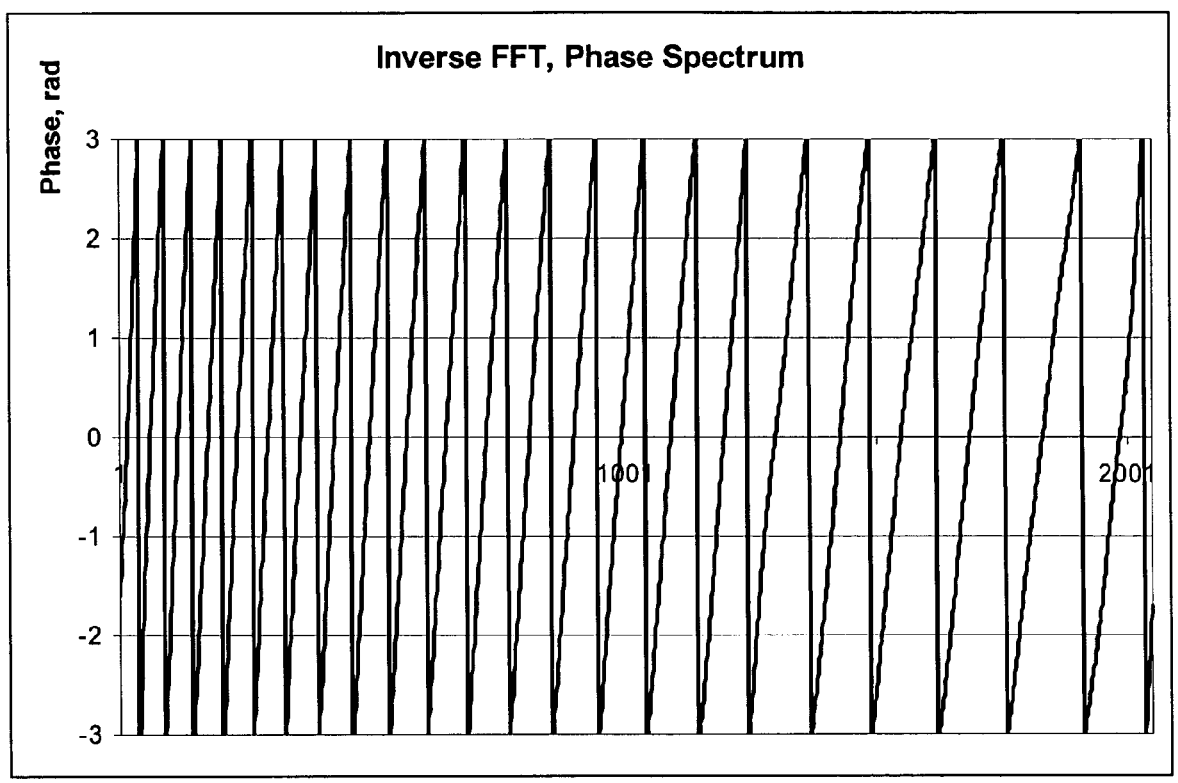
FIG. 11 is a plot of the phase spectrum after inverse FFT of the signal of FIG. 10.

According to the present invention, the phase of the interfered spectrum is defined by applying the inverse FFT to the filtered signal in a complex form. A calculated phase spectrum for an example considered hereafter is shown in FIG. 11. The phase oscillates from $-\pi$ to $+\pi$ corresponding to the number and location of the fringes in the normalized spectrum (see FIG. 8).

Figure 12:
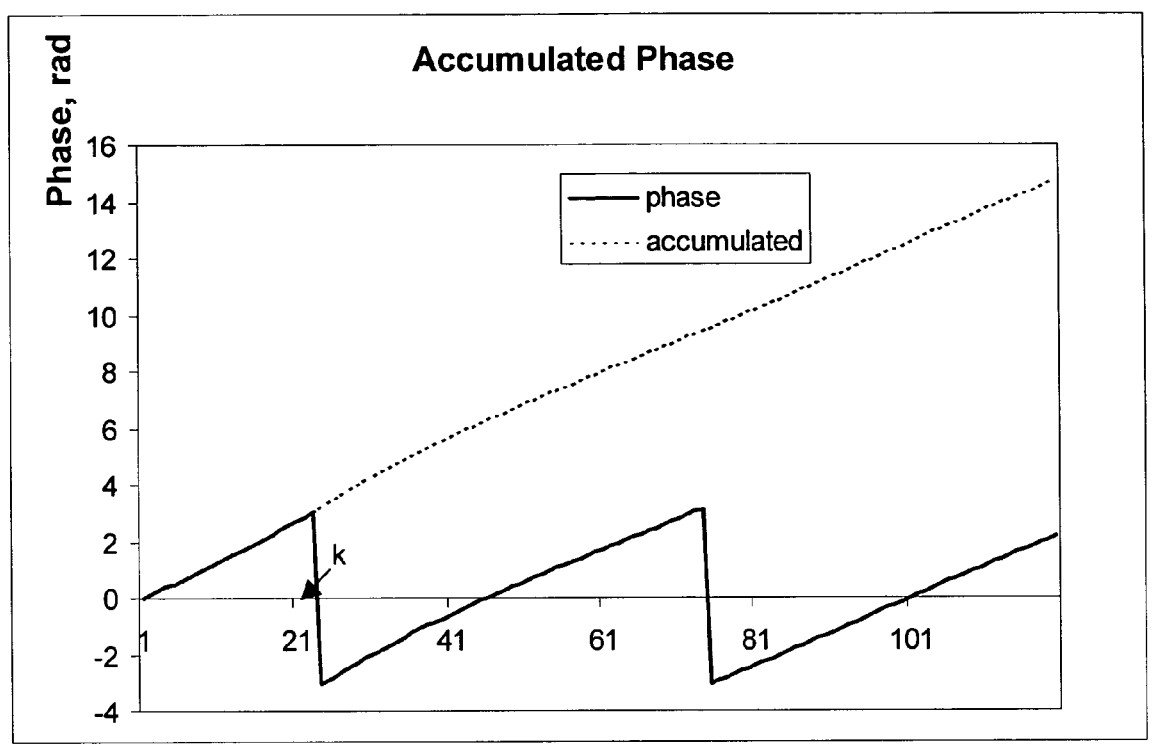
FIG. 12 is an expanded view of FIG. 11 with the plot of the accumulated phase.

Yet according to the present invention, the measured parameter is determined from the accumulated phase. The accumulated phase can be calculated in a variety of ways. Preferably, the accumulated phase is calculated from a fixed value of phase. Such a value can be zero or any other value within the range from $-\pi$ to $+\pi$. For a fixed zero value, an example of calculating the accumulated phase is shown in FIG. 12. The solid line represents the phase described by FIG. 11 starting at $\phi=0$. The phase function has distinctive maxima as values approach $+\pi$. If the first maximum occurs at the point k and it has a value of $\phi_k$, the next value of phase at point k+1 is calculated as a sum:

$$\phi_{k+1}=\phi_k+2\pi$$

until the next maximum is reached where the procedure is repeated and the value of $4\pi$ is added to the phase. The accumulation continues until all oscillating values of phase are corrected by factors of $2\pi$. The number of iterations is equal to the number of fringes which typically numbers from 10 to 50, depending on the OPD and the design of the sensor.

Figure 13:
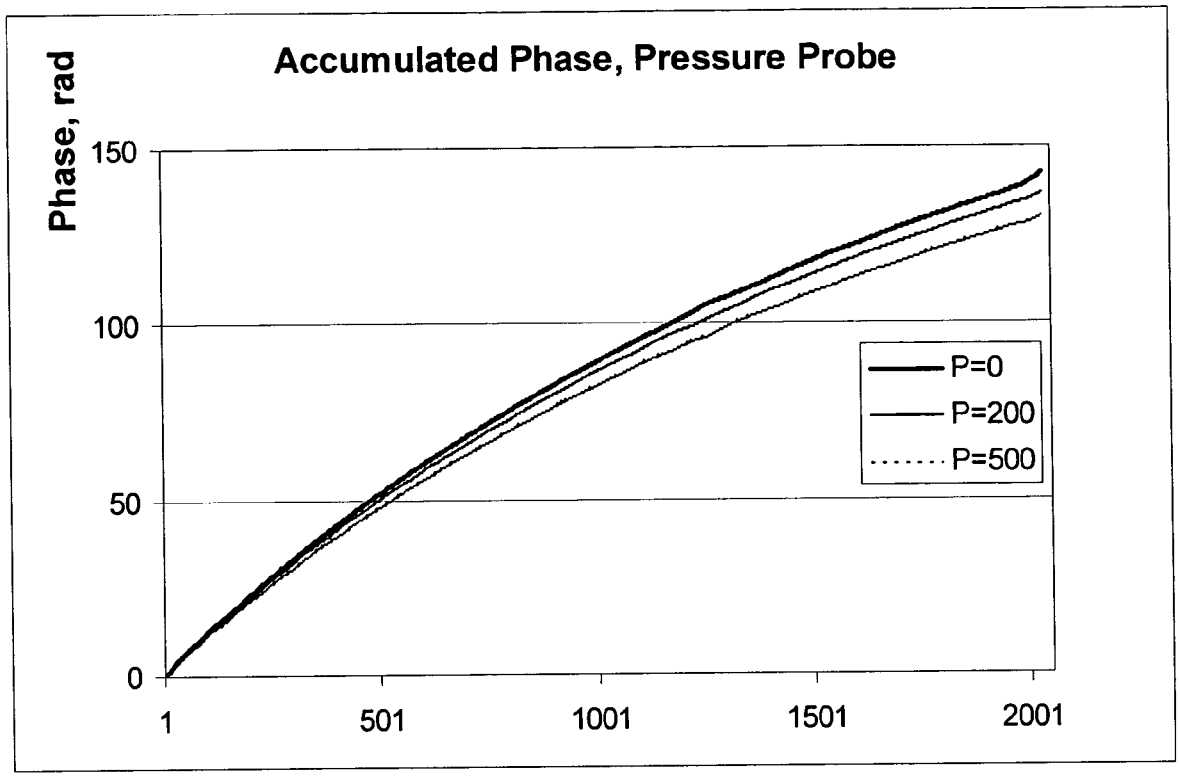
FIG. 13 represents an example of three accumulated phases calculated for three different pressures: 0, 200, and 500 psi.
Figure 14:
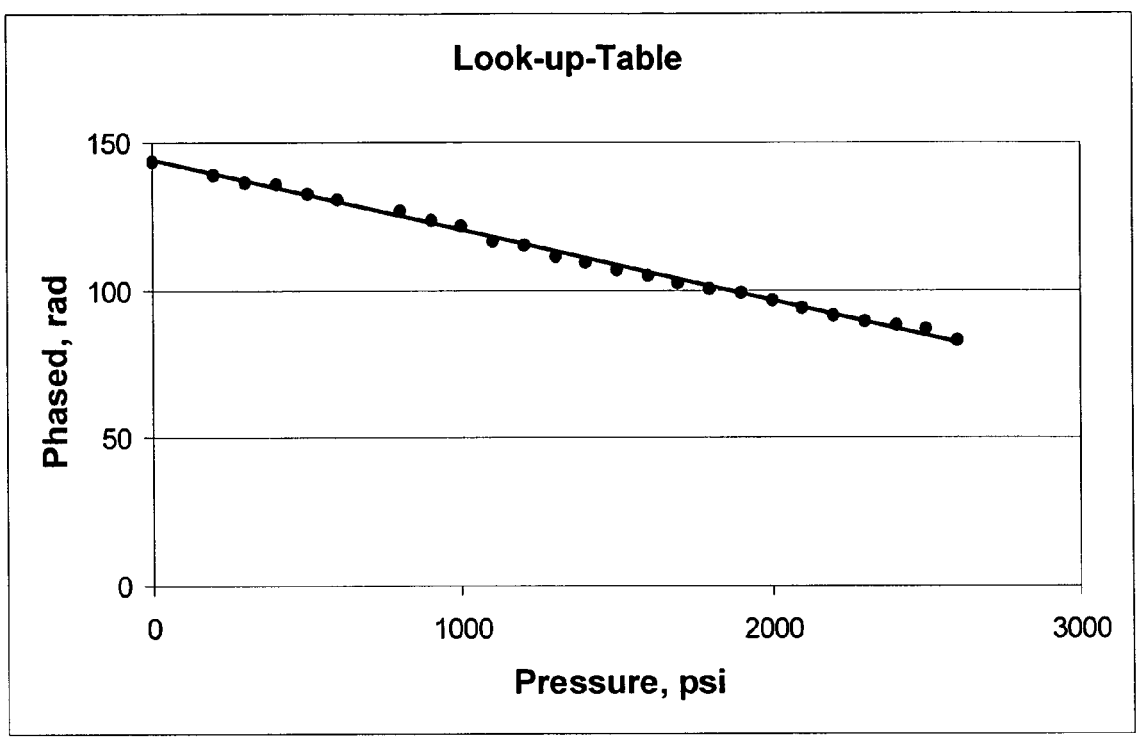
FIG. 14 is a view of the look-up-table of the pressure sensor of FIG. 13. The look-up-table represents the accumulated phase calculated for the last pixel of the spectroscope (k=2048) as a function of the calibrated pressure.

The accumulated phase represents a curve monotonically rising over the number of pixels, which is equivalent to the number of modulation periods of the wavelength spectrum registered by the spectroscope. FIG. 13 shows three such curves calculated for P=0, 200, and 500 psi, respectively. The largest change of phase takes place at the highest points or longest detectable wavelengths. FIG. 14 shows the final accumulated phase calculated at k=2048 for different pressures ranging from P=0 to P=2,700 psi. There is a good linear fit between the accumulated phase and the measurand covering a large dynamic range. This linear fit can be used as a look-up-table representing the relationship between the accumulated phase and measuring parameter. The look-up-table is built during calibration of the device.

Figure 15A:
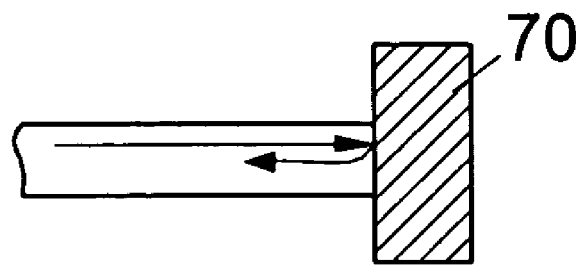
FIG. 15A is a view of the reflective normalization probe according to one embodiment of the present invention.
Figure 15B:
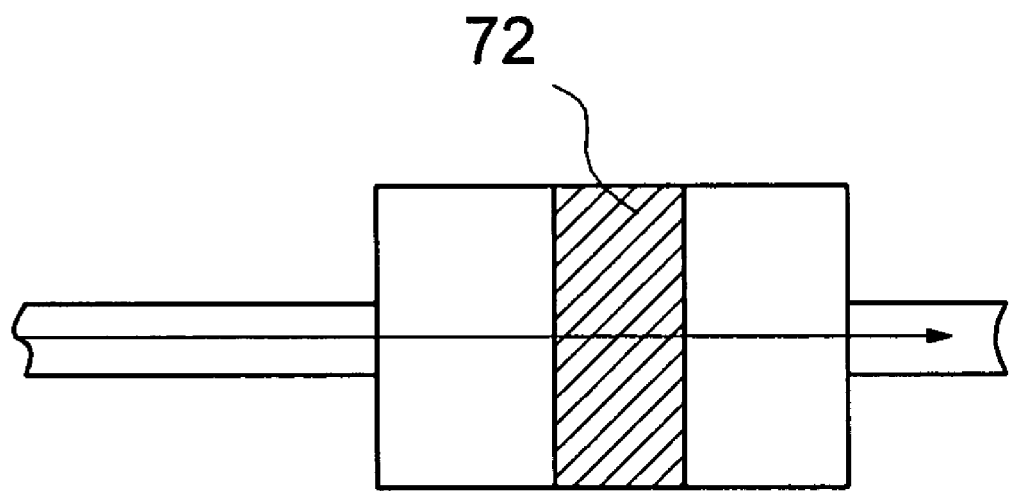
FIG. 15B is a view of the transmittive normalization probe according to another embodiment of the present invention.

Referring back to FIG. 1, a method and a fiber optic device for measuring the physical parameter is disclosed in which a normalization procedure is provided. The normalization procedure is carried out after the installation of the device. Before coupling the measuring interferometric probe, a normalization probe (42) is attached to the connector (18). Preferably, the normalization probe uses the same length of fiber as the measuring probe in order to minimize the coupling mode difference. In one embodiment, the normalization probe can have a reflective surface (70) attached to the fiber end as is shown in FIG. 15A. The coefficient of reflection could be very close to the maximum reflection of the sensing interferometer. In the example above (see FIG. 3), the maximum reflection is approximately 70%. In this case, the recorded spectrum from the probe will adequately represent the polychromatic light source as was shown in FIG. 4. The recorded spectrum is stored in the DSP memory or in a memory buffer, and recalled as $I_{LS}(\lambda)$ data for calculating the normalized spectrum. It is preferable to use a transmittive normalization probe if used for normalizing a transmittive measuring probe. As is shown in FIG. 15B, the transmittive normalization probe may represent a spacing (72) that attenuates the divergent light or a medium that transmits the light with the same efficiency as the measuring probe.

Thus as it was shown by means of the examples above, the proposed interferometric method and a fiber optic device utilizing this method allows for the measurement of a physical parameter over a wide operating range, which shifts the modulated spectral pattern over a large number of spectral fringes. Furthermore, the described method and device can measure the physical parameter with high accuracy, equivalent to short-ranging methods working within one interferometric fringe.

Although the present invention has been described by way of examples thereof, it should be pointed out that any modifications to these examples, within the scope of the appended claims, are not deemed to change or alter the nature and scope of the present invention.

What is claimed is:

1. A fiber optic sensing device for measuring a physical parameter comprising:
    a polychromatic light source, generating light over a wide optical spectrum;
    a fiber optic measuring probe for modulating said polychromatic light, said fiber optic measuring probe having an optical path which is changed with said physical parameter;
    a normalization probe for attenuating said polychromatic light, said normalization probe having an attenuation approximately equal to an attenuation of said fiber optic measuring probe;
    an optical spectrometer means for determining a measurement spectrum of said modulated light and a normalization spectrum of said attenuated light;
    fiber optic means for coupling said modulated light from said fiber optic measuring probe and for coupling said attenuated light from said normalization spectrum to said optical spectrometer;
    a signal processing means for calculating a normalized spectrum from said measurement and normalization spectrums, for calculating a phase of said normalized spectrum to determine the optical path of said fiber optic measuring probe, and for calculating the value of said physical parameter.

2. A fiber optic sensing device according to claim 1, wherein:
    said optical spectrometer means is a diffractive grating based spectrometer with a CCD photodetector array.

3. A fiber optic sensing device according to claim 1, wherein:
    said optical spectrometer means is a diffractive grating based spectrometer with a CMOS photodetector array.

4. A fiber optic sensing device according to claim 1, wherein:
    said optical spectrometer means is a spectroscope based on a variable attenuation filter.

5. A fiber optic sensing device according to claim 1, wherein:
    said signal processing means includes memory for storing calibrated look-up-table data.

6. A fiber optic sensing device according to claim 5, wherein:
    said phase is determined by performing a Fourier transform of said spectrum, digital filtering of said transformed signal by using a band-pass filter, performing an inverse Fourier transform of said filtered signal, determining the phase from said inverse Fourier transform, calculating the accumulated phase from said phase, comparing said accumulated phase with a look-up-table data stored in said memory.

7. A fiber optic sensing device according to claim 1 wherein the fiber optic measuring probe comprises a Fabry-Perot sensing interferometer having a Fabry-Perot cavity which modulates said polychromatic light passing therethrough.

8. A fiber optic sensing device for measuring a physical parameter comprising:
    a polychromatic light source, generating light over a wide optical spectrum;
    a fiber optic measuring probe including a Fabry-Perot sensing interferometer, modulating said polychromatic light by passing it through a Fabry-Perot cavity, having an optical path which is changed with said physical parameter;
    an optical spectrometer means for determining the spectrum of said modulated light in wavelength domain, and fiber optic means for coupling said modulated light from said interferometer to said optical spectrometer;
    a signal processing means for calculating a phase of said spectrum to determine the optical path of said Fabry-Perot cavity, and subsequent means for calculating the value of said physical parameter; and,
    a normalization probe which is attached to said fiber optic means instead of said fiber optic Fabry-Perot measuring probe for purpose of measuring the normalization spectrum;
    said normalization probe has the same light attenuation as said fiber optic Fabry-Perot measuring probe.

9. A fiber optic sensing device according to claim 8, wherein:
    said digital signal processing means records the spectrum from said normalization probe;
    a measuring probe with a Fabry-Perot cavity is connected to said fiber optic means;
    said Fabry-Perot cavity is disposed into a measuring environment; said digital processing means calculates the normalized spectrum by dividing the spectra from said fiber optic measuring probe and said normalization probe.

10. A fiber optic sensing device according to claim 8, wherein:
said digital signal processing determines the phase of said normalized spectrum.

11. A fiber optic sensing device according to claim 10, wherein:
said phase is determined by performing a Fourier transform of said normalized spectrum, digital filtering of said transformed signal by using a band-pass filter, performing and inverse Fourier transform of said filtered signal, determining the phase from said inverse Fourier transform, calculating an accumulated phase from said phase, comparing said accumulated phase with a look-up-table data stored in said memory.

12. A fiber optic sensing method for measuring a physical parameter, comprising steps of:
installing a fiber optic means coupling a polychromatic light source to a connector, which is outside of the measuring environment;
recording a normalization spectrum of said polychromatic light source by an optical spectrometer means with a digital signal processing means outside the measuring environment;
recording a measuring spectrum of polychromatic light source by said optical spectrometer with a digital signal processing means inside the measuring environment;
calculating a normalized optical spectrum;
calculating a phase of said normalized optical spectrum;
giving a value of a physical parameter by comparing said phase with a phase recorded under calibrated conditions.

13. A fiber optic sensing method for measuring a physical parameter according to claim 12, wherein said recording a normalization spectrum further comprising steps of:
attaching a normalization probe to said connector outside the measuring environment;
illuminating said normalization probe with said polychromatic light;
recording a normalization spectrum by said optical spectrometer means;
storing said normalization spectrum in a memory of said digital processing means.

14. A fiber optic sensing method for measuring a physical parameter according to claim 12, wherein said recording a measuring spectrum further comprising steps of:
replacing said normalization probe with a fiber optic Fabry-Perot measuring probe;
installing said fiber optic Fabry-Perot measuring probe into the measuring environment illuminating said fiber optic Fabry-Perot measuring probe with said polychromatic light;
recording a measuring spectrum by said optical spectroscope means;
calculating a normalized spectrum by dividing said measuring spectrum by said normalization spectrum.

15. A fiber optic sensing method for measuring a physical parameter according to claim 13, wherein determining of said phase further comprising steps of:
performing a Fourier transform of said normalized spectrum;
digital filtering of said transformed signal by using a band-pass filter;
performing an inverse Fourier transform of said filtered signal;
determining a phase spectrum from said inverse Fourier transform;
calculating an accumulated phase from said phase.

16. A fiber optic sensing method for measuring a physical parameter according to claim 15, wherein minimum and maximum frequencies of said band-pass filtering are chosen from maximum and minimum of interferometric fringe spacing occurred for minimum and maximum optical path differences.

* * * * *